(12) United States Patent
Burns et al.

(10) Patent No.: US 10,878,064 B2
(45) Date of Patent: Dec. 29, 2020

(54) CLINICAL DATA MANAGEMENT SYSTEM

(71) Applicant: ICON Clinical Reserch Limited, Dublin (IE)

(72) Inventors: Colin Thomas Burns, Maynooth (IE); Gareth Allan Milborrow, Durham (GB); Paul Crean, Newbridge (IE); Michael Grossman, San Mateo, CA (US)

(73) Assignee: ICON CLINICAL RESEARCH LIMITED, Dublin (IE)

( * ) Notice: Subject to any disclaimer, the term of this patent is extended or adjusted under 35 U.S.C. 154(b) by 568 days.

(21) Appl. No.: 15/653,385

(22) Filed: Jul. 18, 2017

(65) Prior Publication Data
US 2017/0316183 A1  Nov. 2, 2017

Related U.S. Application Data

(63) Continuation of application No. 13/792,854, filed on Apr. 2, 2013, now Pat. No. 9,740,831.
(Continued)

(51) Int. Cl.
*G06F 19/00* (2018.01)
*G16H 10/20* (2018.01)
(Continued)

(52) U.S. Cl.
CPC .............. *G06F 19/36* (2013.01); *G16H 10/20* (2018.01); *G06F 16/212* (2019.01); *G06F 16/254* (2019.01)

(58) Field of Classification Search
CPC .......... G06F 17/00; G06F 17/60; G06F 17/30; G11C 7/00
(Continued)

(56) References Cited

U.S. PATENT DOCUMENTS 7,054,823 B1 * 5/2006 Briegs ................ G06F 19/36
705/2
7,089,247 B2 * 8/2006 Kloos ................ G06F 19/326
(Continued)

FOREIGN PATENT DOCUMENTS

| WO | 2009/155558 | 12/2009 |
| WO | 2011/127249 | 10/2011 |
| WO | 2012/092589 | 7/2012 |

OTHER PUBLICATIONS

Google patents search, Apr. 21, 2017.
EAST search, Apr. 21, 2017.

*Primary Examiner* — Dilek B Cobanoglu
(74) *Attorney, Agent, or Firm* — Bookoff McAndrews, PLLC

(57) ABSTRACT

A clinical data management system has databases, processors in servers which are programmed to process clinical data and communicate with user interfaces and external systems interfaces, and at least one database. The system imports source data from disparate clinical site sources into staging databases at refresh intervals, maintains data models, and maps data from the staging databases into the data models, and feeds data from the data models into data delivery databases. There is a uniform refresh frequency for the staging databases. The system output is regularly updated data for clinical site performance, quality and risk metrics to a clinical study team. The data mapper servers identify each of a plurality of source data stages, and transform data from each stage to one or more data models according to one or more mapsets, each mapset defining a transformation.

22 Claims, 14 Drawing Sheets

Related U.S. Application Data

(60) Provisional application No. 61/609,482, filed on Mar. 12, 2012, provisional application No. 61/609,473, filed on Mar. 12, 2012.

(51) Int. Cl.
*G06F 16/21* (2019.01)
*G06F 16/25* (2019.01)

(58) Field of Classification Search
USPC .................................. 705/2; 707/10, 100
See application file for complete search history.

(56) References Cited

U.S. PATENT DOCUMENTS

| | | | | |
|---|---|---|---|---|
| 7,117,215 | B1 * | 10/2006 | Kanchwalla | G06F 16/283 707/602 |
| 7,191,183 | B1 * | 3/2007 | Goldstein | G06Q 50/22 707/602 |
| 8,041,581 | B2 * | 10/2011 | Mitchel | G06F 16/93 705/2 |
| 2004/0249664 | A1 * | 12/2004 | Broverman | G16H 10/20 705/2 |
| 2005/0071194 | A1 * | 3/2005 | Bormann | G06Q 50/22 705/2 |
| 2005/0228808 | A1 * | 10/2005 | Mamou | G06F 16/254 |
| 2012/0290317 | A1 * | 11/2012 | Nair | G16H 50/70 705/2 |

\* cited by examiner

```
PROC SQL;
    INSERT INTO WORK.DM
        (STUDYID
            ,DOMAIN
            ,USUBJID
            ,SUBJID
            ,RFSTDTC
            ,RFENDTC
            ,RFICDTC
            ,SITEID
            ,BRTHDTC
            ,AGE
            ,AGEU
            ,ARMCD
            ,ARM
            ,DMDTC
            ,DMDY
            ,RACEOTH
        )
    SELECT
        DM.STUDY AS STUDYID
        ,'DM' AS DOMAIN
        ,CATX('-', DM.STUDY, SUBSTR(DM.INVSITE, 8, 3), DM.PT) AS USUBJID
        ,DM.PT AS SUBJID
        ,%CREATEISODATE(RA.RADAT_FUL) AS RFSTDTC
        ,%CREATEISODATE(ST.STCDAT_FUL) AS RFENDTC
        ,%CREATEISODATE(IC.DSSDAT) AS RFICDTC
        ,SUBSTR(DM.INVSITE, 8, 3) AS SITEID
        ,%CREATEISODATE(DM.BRTHDAT_FUL) AS BRTHDTC
        ,%SUBDATES(%CREATEISODATE(DM.BRTHDAT_FUL), %CREATEISODATE(RA.RADAT_FUL), YEAR') AS AGE
        ,'YEARS' AS AGEU
        ,RA.RATL_FUL AS ARMCD
        ,RA.RATL_DLV AS ARM
        ,%CREATEISODATETIME(VIS.VISDAT_FUL, VIS.VISTIM) AS DMDTC
        ,%CREATESTUDYDY(%CREATEISODATETIME(VIS.VISDAT_FUL, VIS.VISTIM), %CREATEISODATE(RA.RADAT_FUL)) AS DMDY
        ,DM.RACEOTH_FUL AS RACEOTH
FROM SRC.DM A LEFT JOIN SRC.RA B ON A.PT = B.PT
LEFT JOIN SRC.VIS C ON A.PT= C.PT AND A.VISIT_NUMBER = C. VISIT_NUMBER
LEFT JOIN SRC.ST D ON A.PT = D.PT
LEFT JOIN SRC.IC E ON A.PT = E.PT;
```

Fig.11

| | | | | | |
|---|---|---|---|---|---|
| HUB.DM.STUDYID | = | SRC.DM.STUDY | | | |
| HUB.DM.DOMAIN | = | DM | | | |
| HUB.DM.SUBJID | = | SRC.DM.PT | | | |
| HUB.DM.SITEID | substr | SRC.DM.INVSITE | 8 | 3 | |
| HUB.DM.USUBJID | catx | '-' | HUB.DM.STUDYID | HUB.DM.SITEID | HUB.DM.SUBJID |
| HUB.DM.RFSTDTC | %createISOdate | SRC.RA.RADAT_FUL | | | |
| HUB.DM.RFENDTC | %createISOdate | SRC.ST.STCDAT_FUL | | | |
| HUB.DM.BRTHDTC | %createISOdate | SRC.DM.BRTHDAT_FUL | | | |
| HUB.DM.AGE | %subDates | HUB.DM.BRTHDTC | HUB.DM.RFSTDTC | YEAR' | |
| HUB.DM.SEX | %VLAutoMap | SRC.DM.SEX | CODE_TO_CODE | | |
| HUB.DM.RACE | %VLAutoMap | SRC.DM.RACE | CODE_TO_CODE | | |
| HUB.DM.DMDTC | %createISOdatetime | SRC.VIS.VISDAT_FUL | SRC.VIS.VISTIM | | |
| HUB.DM.DMDY | %createSTUDYDY | HUB.DM.DMDTC | HUB.DM.RFSTDTC | | |
| HUB.DM.RFICDTC | %createISOdate | SRC.IC.DSSDAT | | | |
| HUB.DM.ARM | = | SRC.RA.RATL_DLV | | | |
| HUB.DM.ARMCD | = | SRC.RA.RATL_FUL | | | |
| HUB.DM.RACEOTH | = | SRC.DM.RACEOTH_FUL | | | |
| JOIN | from src .DM a left join src.RA b on a.PT = b.PT<br>left join src.vis c on a.PT= c.PT and a.VISIT_NUMBER = c. VISIT_NUMBER<br>left join src.st d on a.PT = d.PT<br>left join src.ic e on a.PT = e.PT | | | | |

Fig.12

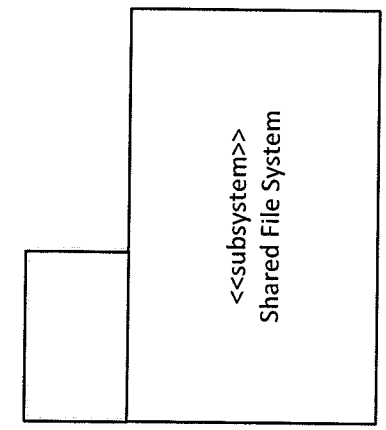
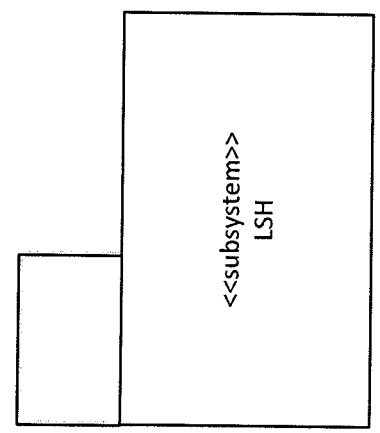
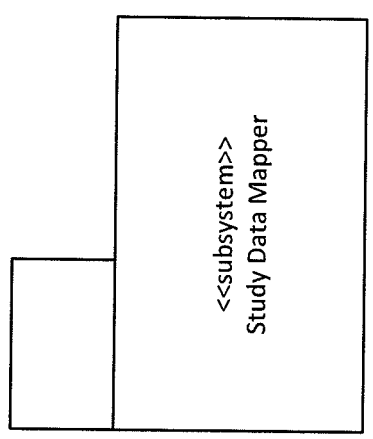
Fig.13
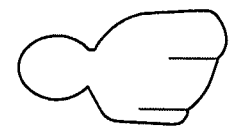
Standards Review Board
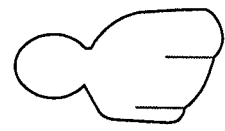
Sponsor
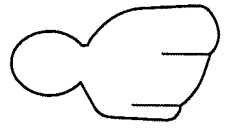
Vaildator
Fig.14
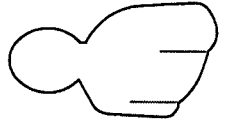
Mapping Author
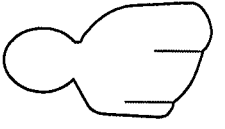
Data manager

CLINICAL DATA MANAGEMENT SYSTEM

RELATED APPLICATION(S)

This application is a continuation of U.S. application Ser. No. 13/792,854, filed Apr. 2, 2013 which claims priority to U.S. Provisional Application No. 61/609,482 filed Mar. 12, 2012, and 61/609,473, filed Mar. 12, 2012 each of which is hereby incorporated by reference herein in their entireties.

FIELD OF THE INVENTION

The invention relates to the technical data management aspects of conducting clinical trials.

PRIOR ART DISCUSSION

For approval of a new drug it is necessary for clinical trials to be carried out in a large number of sites, typically in a large number of countries.

This gives rise to the technical problems of correctly mapping, interpreting, and analysing data from various sources, each having a particular bias or number of biases.

WO2009/155558 (Webber) describes an approach in which different tables are updated in response to data from an associated shared server interacting application. Related publication US2010/0228699 describes aspects of allowing clinical trial organisations to access shared databases.

U.S. Pat. No. 8,041,581 (Mitchel) describes a method in which there is automatic transfer of an electronic read-only clinical trial source document to a trusted third party server.

US2012/0290317 (Nair et al) discloses a management tool to store queries and results for a multiple tagged clinical trial database.

WO2011/127249 (Nextdocs Corp) discloses maintenance of a web site for each clinical trial, and a investigator portal for each clinical investigator, enabling him or her to monitor activities.

U.S. Pat. No. 7,054,823 (Schering Corp.) discloses use of a main database of data pertaining to previous clinical trials and resources for future trials.

WO2012/092589 (Accenture Global Services Ltd.) discloses a clinical quality analytics system with a process map toolset which determines a process map from a protocol for medical treatment guidelines.

The present invention is directed towards providing a clinical data management system in which there is improved data processing directed towards achieving improved:
  transparency across the different studies, and/or
  improved extend and integrity of risk profile data per site, and/or
  data monitoring investigation productivity, and/or
  earlier identification of lapses in scientific rigour and protocol adherence.

SUMMARY OF THE INVENTION

According to the invention, there is provided a clinical data management system comprising at least one digital data processor, user interfaces and external system interfaces, and at least one database, wherein the data processor is adapted to:
  (a) import source data from disparate clinical site sources into staging databases at refresh intervals,
  (b) maintain a plurality of data models, and a mapper mapping data from the staging databases into the data models, and
  (c) the mapper mapping data from the data models into data delivery databases.

In one embodiment, the mapper is adapted to perform said step (b) mapping by:
  identifying each of a plurality of source data stages, and transforming data from each stage to one or more data models according to one or more mapsets.

In one embodiment, each mapset defines a transformation. In one embodiment, the mapper is adapted to uses metadata defining the data models for interfacing with the models.

In one embodiment, the system is adapted to perform step (a) at a refresh frequency which is uniform.

Preferably, the system is adapted to perform step (c) for the purposes of providing regularly updated site performance, quality and risk metrics to a clinical study team.

In one embodiment, the processor is adapted to capture and maintain an audit trail of source data imported into the staging databases. In one embodiment, the processor is adapted to manage clinical study level staging databases and also pooled cross-study level data.

In one embodiment, the processor is adapted to inter-link the data models. Preferably, the processor is adapted to manage a study metadata model, a clinical data model, and a system and discrepancy data model, and a reporting support data model. In one embodiment, the processor is adapted to manage relationships between said models.

In one embodiment, n the processor is adapted to transform data into the clinical data model if it complies with a recognised standard, and into the discrepancy data model if not. Preferably, the processor is adapted to initially map data to the clinical data model and to then map it to the discrepancy data model if it is non-standard. In one embodiment, the processor is adapted to relate non-standard variables to a parent domain and to create supplementary data sets on-the-fly. Preferably, the processor is adapted to add unique identifiers to tables to identify change deltas.

In one embodiment, the processor is adapted to add original code and decode values to support data cleaning. In one embodiment, the processor is adapted to add common data status flags for status and query management. In one embodiment, the processor is adapted to insert derivations to support known downstream analysis and reporting, and a source reference field to enable traceability from raw source data to conformed data.

In one embodiment, the processor is adapted to insert extensions to date fields where imputations are required for incomplete or invalid dates.

In another embodiment, the processor is adapted to provide in each table of the clinical data models a primary key and a surrogate key, in which a primary key is a combination of columns or rows which define the uniqueness of a record within a table, and a column or row which is a member of a primary key cannot contain null values.

In another embodiment, the system is adapted to define primary keys within the clinical data models as mutable, in which the data values stored in the constituent variables may change, and in which a surrogate key is a single row or column that uniquely identifies a record in a table and are immutable and cannot contain null values.

In one embodiment, the data models include a standard data model to act as consistent core structures of data across all studies, to allow for study-specific additions, but do not allow for any destructive changes to core variables or tables. Preferably, the data models are in a hierarchy consisting of three levels; first and second levels of standard models and a third level for study implementation. In one embodiment, the first level includes version-controlled metadata definitions of the core data models, the second level includes metadata definitions of sponsor standard data models, and the third level includes study execution physical data models.

In one embodiment, a study metadata model contains study level metadata describing study design and planning, and also clinical reference tables.

In one embodiment, a clinical data visualisation model includes a study-level standard reporting structure for data visualisation through third party reporting tools.

In a further embodiment, a data model includes a subject snapshot table and a listings table per domain, and the subject snapshot table contains a row for each subject describing their current status and progress to date in the study, with a combination of demography data, disposition or milestone data, eligibility data, and safety data. Preferably, the metadata is in a metadata model. In one embodiment, the processor is adapted to perform two transformations according to the same mapset, comparing resultant target data, and providing feedback.

In one embodiment, at least two mapper software instances independently specify transformations to be applied as part of the mapping process, and a mapping reviewer function automatically generates a detailed report of the differences between two different specified transformations.

In one embodiment, the source data is clinical study data and the reviewer generates a detailed report on the compliance mapping with its selected standards.

In one embodiment, the mapping reviewer is adapted to release each map in a mapset as soon as it is complete, and to release an entire mapset when its component maps are complete; and wherein the metadata comprises a library of pre-defined mapping functions that can be applied to variables; and wherein the metadata is used to automatically generate mapping software functions.

In a further embodiment, a mapset includes maps and sub-maps; wherein a sub-map table alias is used to identify how a sub-map relates to a set of variables that are contained in a common sub-map. In one embodiment, each mapset has an associated set of source and target tables; wherein a mapset defines transformation of source variables, said variables including data, fields, properties, attributes, and table value lists; and wherein the transformation step maps targets to a source.

In a further embodiment, the processor is adapted to perform the step of mapping from one or more source structures to a target structure according to a table map.

In one embodiment, there are multiple combinations of source structures that are mapped to a single target structure and the method creates multiple maps to the same target, called submaps; wherein common variables in separate submaps are named the same and have the same mapping requirements, and these common variables are mapped the same way in a common mapping and are applied to each submap within a sub map group. In one embodiment, a search engine of the system is adapted to identify similar previously mapped table structures as exact or partial matches.

In one embodiment, the system is adapted to perform the step of applying system installation configurable attributes or tags to mapping projects, table sets, value lists, variables, table maps, submaps, or variable maps that can then be used for searching and reporting on any of said entities.

In one embodiment, code is generated in multiple languages for the same mappings giving the same resultant data.

In another aspect, the invention provides a computer readable medium comprising software code to perform operations of a system as defined above in any embodiment when executed by a digital processor.

DETAILED DESCRIPTION OF THE INVENTION

Brief Description of the Drawings

The invention will be more clearly understood from the following description of some embodiments thereof, given by way of example only with reference to the accompanying drawings in which:

FIG. 11 is a sample of transform code generated by the study data mapper, based on mappings captured in the system;

FIG. 12 details a specification captured by an end-user to generate the transform code in FIG. 11;

FIG. 13 is a block diagram showing interaction of the study data mapper with other systems in the overall clinical data management system;

FIG. 14 details the user actors that interact with the system; and

DESCRIPTION OF THE EMBODIMENTS

Figure 1:
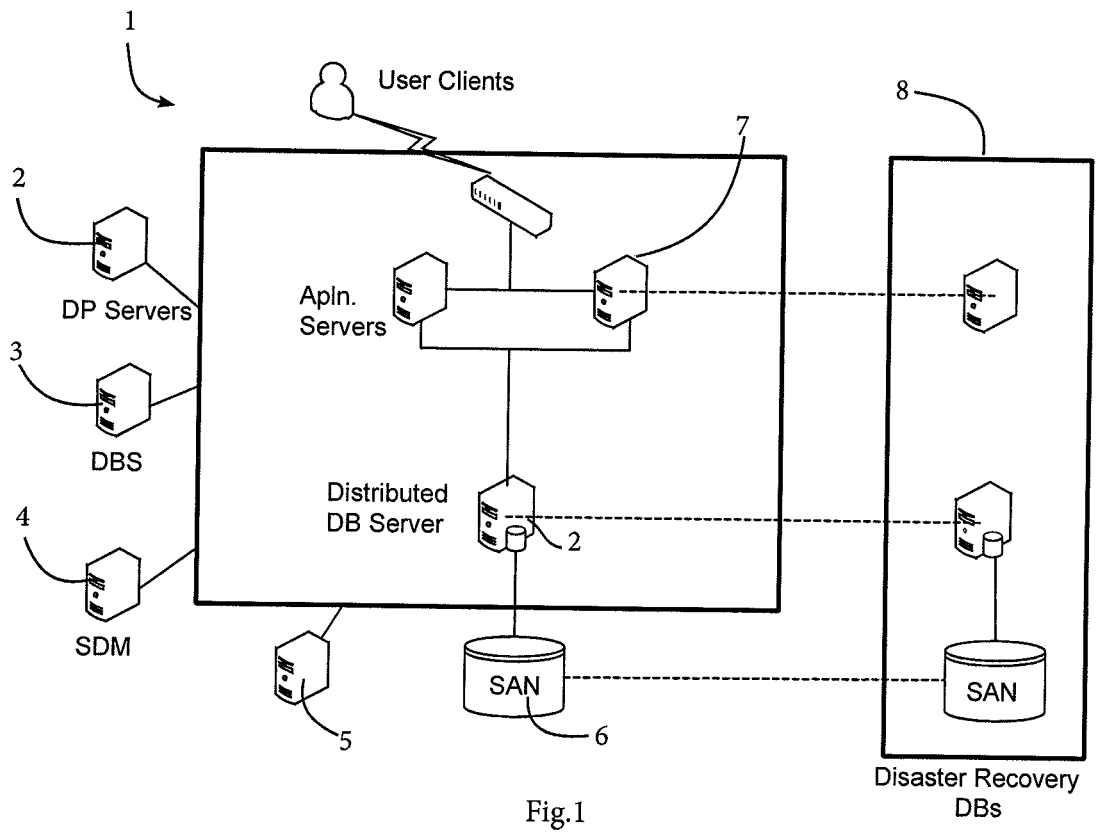
FIG. 1 is a high-level block diagram showing hardware architecture of a clinical data management system of the invention.

FIG. 1 is a block diagram of the hardware architecture of a clinical data management system of one embodiment. The system 1 comprises distributed processing ("DP") servers 2, a database server 3, a staging database 4, a data warehouse 5, a storage area network (SAN) 6, an application servers 7, and a backup system 8 for database recovery. The system 1 performs centralisation and standardisation of clinical data processing and data access. Because of the diversity of data consumers and their clinical data requirements, a single physical data model cannot meet all requirements effectively.

The system 1 implements a clinical data lifecycle which comprises multiple physical data models at the individual study level to provide flexibility and performance. The data models are designed to reflect the requirements of their intended target audience, with particular focus on providing data structures that perform well with their intended data presentation tool.

Common data derivations, standardisations, conversions, coercions, and imputations that are made during the data lifecycle are performed once and the resulting value is reused by all downstream data users/structures; derivations are not to be recalculated or imputed.

Data structures containing pools of combined data are maintained at the program and sponsor levels for cross-study analysis. Aggregated data structures to support clinical data metrics are also maintained.

Figure 2:
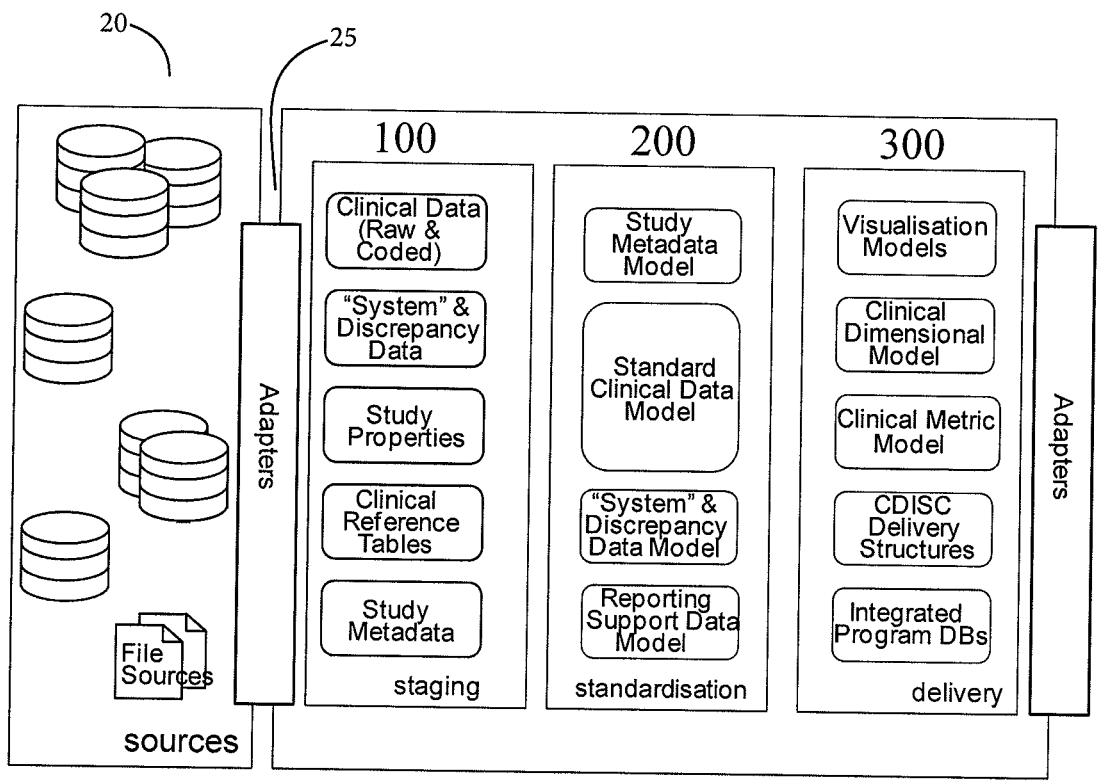
FIG. 2 is a high-level data flow diagram for clinical data acquisition and initial processing.

The main data flows are shown in FIG. 2. Source data is provided by various databases 20 and is written by adapters 25 to staging databases 100. A data mapping system called a "study data mapper" ("SDM") transforms the data from the staging databases 100 to models 200 in a standardisation layer. There is then transfer to data delivery models 300 which provide the results in the various formats and media required.

The system implements a clinical data flow by loading clinical data from source databases 20 on a daily refresh to the staging databases 100. The data mapping system transforms the data daily from the staging databases 100 to the models 200. Data is presented in the data delivery models 300 daily and the end users of the clinical data management system have access to up-to-date clinical data outputs.

Data Staging (100)

The data staging area is a permanent staging area that maintains a full audit history of raw data that has been loaded. There are study-level staging areas for study-level data, and pooled staging areas for cross-study data. The former are important for maintenance of integrity of per-study data. The system 1 loads clinical data from the source databases 20 on a daily refresh to the staging databases 100, however different refresh periods may be used. The staging layer also includes system and discrepancy data, clinical study properties, tables of clinical reference data, and clinical study metadata.

Clinical Data Standardization (200)

The standardisation layer comprises a number of inter-linked data models to act as a standardised access point for all study clinical data.

Model Hierarchy

Figure 3:
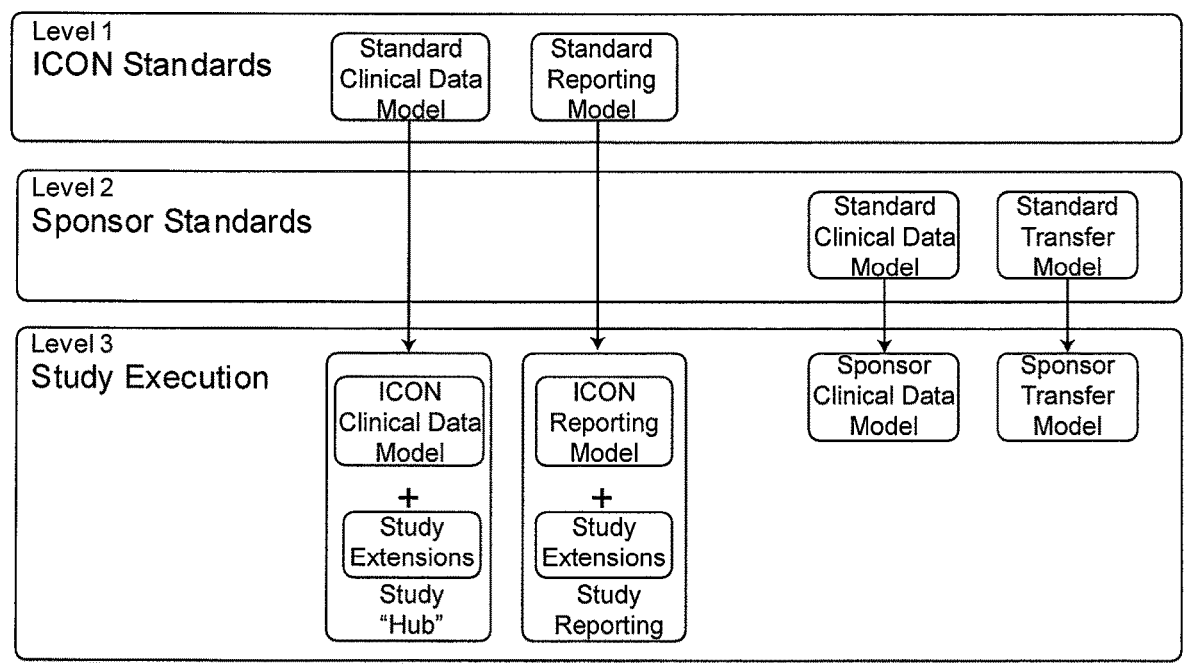
FIG. 3 is a block diagram showing a hierarchy of data models.

The standard data models are designed to act as consistent core structures of data across all studies. These core data models allow for study-specific additions, but do not allow for any destructive changes to core variables or tables. The data model hierarchy consists of three levels; two levels of standard models and a third level for study implementation (FIG. 3):

Level 1 (standards for a clinical research organisation (CRO), called "ICON" in this case): Version-controlled metadata definitions of the ICON core data models.

Level 2 (Sponsor Standards): Metadata definitions of sponsor standard data models.

Level 3 (Study Execution): Physical data models.

In cases where the standard model does not support a study-level variable or domain, an additional variable or domain may be added to the study-level model. This extension must be approved before the variable or domain can be used in production.

Study Metadata Model

The study metadata model uses a central repository of metadata that includes technical metadata describing target data models; tables, table variables, value lists, value list values, version attributes (author, approver, version number, validation status, etc.) and search tags (e.g., therapeutic area, sponsor). Additionally, the study metadata model contains study level metadata describing study design (such as study start up and close details) and planning (e.g., planned events and procedures). Clinical reference tables (such as adverse events of special interest) are also stored as part of this model.

Clinical Data Model

The clinical data model is a study-level data structure within the clinical data standardisation hub 200 ("the hub"). It is designed to store conformed study clinical data in a standard structure. The standard clinical data model was designed with CDISC standards in mind, particularly the SDTM guidelines for domains, variables and naming convention.

A potential disadvantage of using SDTM is the physical implementation of non-standard variables, i.e. the supplemental qualifier concept, in which non-standard variables are added to one or more overflow tables (supplemental qualifier tables), to simplify the delivery of non-standard variables. This implementation, while meeting its design goal, causes problems from an analysis and reporting perspective as these overflow containers are taken into account while designing data queries. This difficulty is further compounded because the structure of the supplemental qualifier tables does not match that of the standard tables.

To improve reusability of standard programs and to aid analytics and reporting, non-standard variables are added directly "to the right" of the related parent domain, and SUPP data sets are created "on the fly" when data is moved from the standard model to SDTM.

The clinical data model is configured as follows:

Stage 1: The SDTM v1.2 data model and associated SDTM v3.1.2 Implementation Guide were used as the foundation for the data model.

Stage 2: Variables were added from the three general observation classes, as well as identifiers and timing variables, except where strictly prohibited by the SDTM v3.1.2 IG or where the intent of the variable contradicted the type of data collected (e.g., IESTDTC and IEENDTC are not included as part of the model as Inclusion/Exclusion Criteria are not collected in this manner).

Stage 3: Supplemental qualifiers as identified in the SDTM v3.1.2 IG were added to their parent domains.

Stage 4: Non-SDTM variables to support known downstream requirements were added; including:

Unique identifiers were added to all tables to identify change deltas.

Original code and decode values were added to support data cleaning.

Common data status flags for CRF status and query status.

Derivations to support known downstream analysis and reporting.

A source reference field to enable traceability from raw data to conformed data.

Extensions to date fields where imputations are required for incomplete/invalid dates Each table in the standard models contains both a primary key and a surrogate key. A primary key is a combination of columns which define the uniqueness of a record within a table. A column which is a member of a primary key cannot contain null values. Primary keys within the standard models are mutable, i.e. the data values stored in the constituent variables may change. A surrogate key is a single column that uniquely identifies a record in a table. Surrogate keys within the standard models are immutable and cannot contain null values. Where there is a single source for a record in a target dataset (a one-to-one mapping), the surrogate key on the target dataset is the unique identifier from the source dataset. Where multiple source records are joined to create a single target record (a many-to-one mapping), standard transformation functions automate the selection of the correct source variable for the target surrogate key. These transformation functions are source system specific.

At least some standard tables contain two timestamp records. If timestamps reflecting record creation and record updates are available in the source data, they will be populated as follows:

SRC_CREATE_TS: The minimum creation timestamp for a source record in the source system. For merged records, this timestamp is the minimum timestamp for the merged records.

SRC_UPDATE_TS: The maximum update timestamp for a source record. For merged records the maximum timestamp from the merged sources is used.

Clinical system & discrepancy data model

This is a study-level data structure designed to store conformed study clinical system and discrepancy data in a standard structure.

Data Model Interoperability in the Standardisation

The data models that comprise the standardisation layer are a mix of relational models and domain models.

Depending on the granularity of the data that is being linked different keys are used:

Study data: A conformed business key is used across models that support study-level reporting. The business key is sourced from a mastered list of studies, and all references to a study in the data standardisation layer must map to this standard value.

Subject data: A system of record is designated from the source systems for the study, and all references to a subject in the data standardisation layer must map to this standard value.

Clinical data: A natural key is defined on all clinical data captured in the study which normally matches the primary key. In the case where the natural key is not truly unique, an artificial key is introduced to guarantee uniqueness.

Discrepancy data: Discrepancy data contains a common natural key with the clinical data, but may be at a lower level of granularity. In this case the data is aggregated to the level of clinical data and matched on natural keys. In the case where the natural key is not truly unique, a common artificial key is identified and used.

As a rule, data queries that run across the models in the clinical data standardisation layer (200) are discouraged. In order to support cross-model analysis and reporting, data delivery structures are available in the data delivery layer (300) that combine data from the clinical, system & discrepancy and metadata standard models.

Data Delivery Models 300

The data delivery models in the delivery layer 300 are re-structured copies of the data that is held in the standardisation layer 200. The data delivery models can be broadly categorised into three types:

standard industry models (e.g. SDTM) and sponsor-specified delivery models, reporting models: including the CDR Clinical Data Lifecycle for SpotFire, and the Clinical Dimensional Model for OBIEE, and aggregated data models: data structures containing aggregated clinical data metrics which are used as a source for other repositories.

The data delivery models in the delivery layer are re-structured copies of the data that is held in the standardisation layer.

Clinical Data Visualisation Model

The clinical data visualisation model is a study-level standard reporting structure in LSH to support data visualisation through third party reporting tools.

The data model consists of a subject snapshot table and a listings table per domain.

The subject snapshot table contains a row for each subject describing their current status and progress to date in the study. The table consists of a combination of demography data, disposition/milestone data, eligibility data, and safety data.

The table design is a non-linear accumulating snapshot.

The listings tables were designed as follows:

Stage 1: The CDR standard clinical data model was used as the foundation for each clinical domain in the data model.

Stage 2: Source system variables such as raw date and internal identifiers were removed.

Stage 3: Standard derivations as identified by the CDR Reporting team were added. These derivations will be moved to CDR standard clinical data model at a later date.

Stage 4: Variables were added to support SpotFire Delta Review, including a unique identifier, a creation timestamp and an update timestamp.

Stage 5: All variables from the subject snapshot table were added as header variables to the domain listing tables.

Each record in the visualisation data model contains a key (RPT_SK) that uniquely identifies a record in the model. These keys are immutable and cannot contain null values.

Each table contains audit fields that can be used to identify change deltas

If timestamps reflecting record creation and record updates are available in the source data, they will be populated as follows:

SRC_CREATE_TS: The minimum creation timestamp for a source record in the source system. For merged records, this timestamp is the minimum timestamp for the merged records.

SRC_UPDATE_TS: The maximum update timestamp for a source record. For merged records the maximum timestamp from the merged sources is used.

SRC_REF: Contains references that can be used to trace raw data sources to the CDR standard data model.

Audit details are maintained for all ETL processes that are run to populate the visualisation date model. All non-snapshot CDR visualisation tables contain two foreign keys to the audit table:

RPT_CREATE_PROC_FK: Links to the audit record of the process that initially loaded a row of data.

RPT_UPDATE_PROC_FK: Links to the audit record of the process that most recently updated a row of data.

Non-snapshot tables contain fields that were added to support SpotFire Delta Review:

RPT_SK: An ID that is unique in a schema/project, rather than unique within the table. This ID is immutable.

RPT_ROW_VERSION: Reflects the number of times that a record was changed based on a change in the source data. If data is reloaded in LSH, but there was no actual change to the source data, this variable will not be updated. Value is set to 1 for initial load, and is incremented by 1 every time a change is reflected in the target table.

Figure 4A:
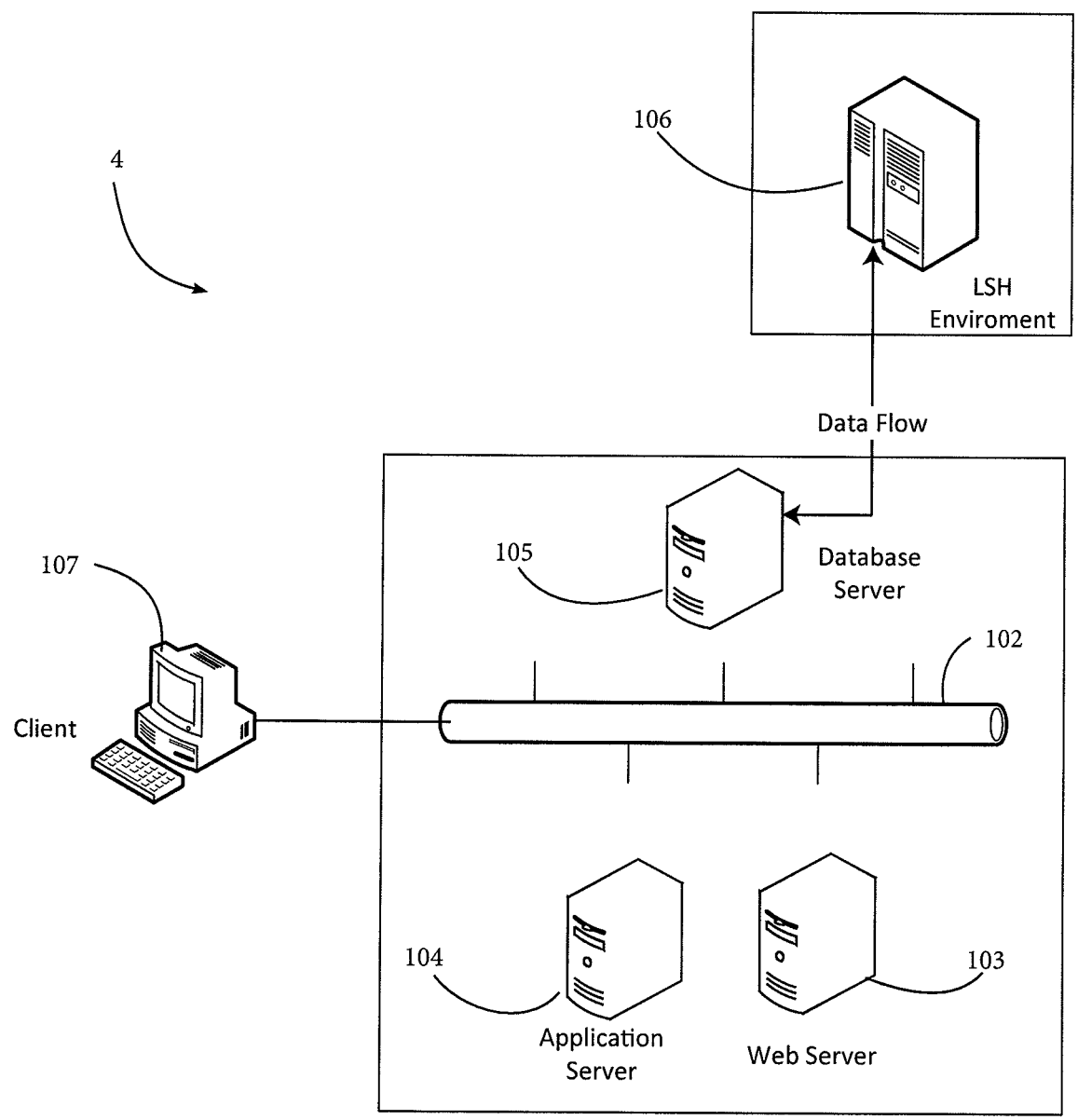
FIG. 4(a) is a block diagram illustrating hardware for a data mapping components of the system.

Referring to FIG. 4(a) the study data mapper ("SDM") system 4 of the overall clinical data management system 1 is implemented on a hardware architecture as illustrated. There is a local network 102, a Windows 2008™ Web server 103, a Windows 2008™ application server 104, and an Oracle 11gr2™ database server 105. There is an interface to a cluster of LSH servers 106, and clients 107 communicate with the network 102 database server.

Figure 4B:
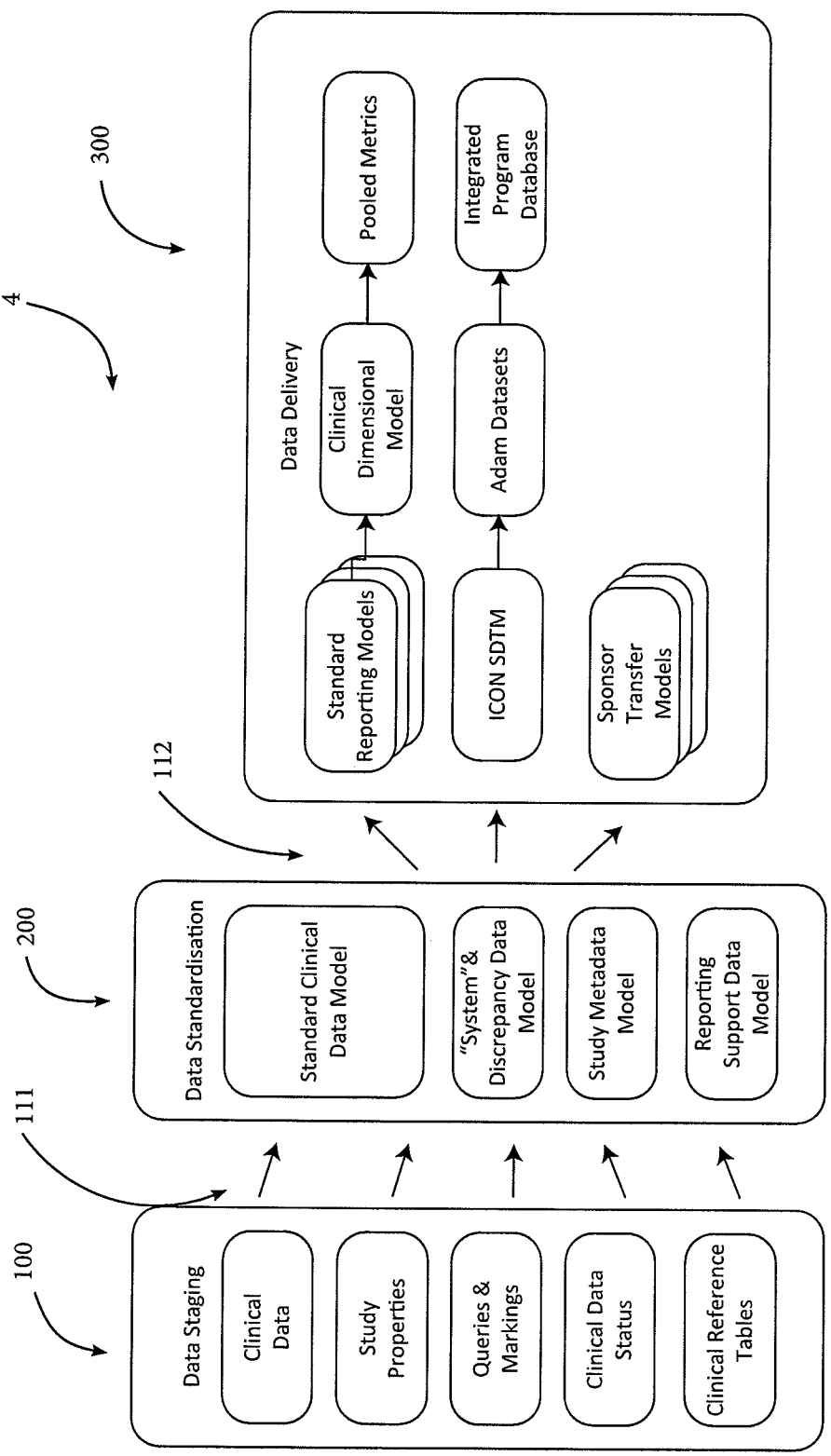
FIG. 4(b) is a flow diagram showing the main data mapping flows implemented by a study data mapper set of software functions of the system.

The SDM 4 is part of the clinical data management system 1, and referring to FIG. 4(b), it has mapping software components 111 operating from the data staging layer 100, and components 112 operating from the data standardisation layer 200 to the delivery layer 300.

The components 111 manage various data sources 100 including clinical data from various sites, clinical study properties, and clinical reference tables. The mapping method maps the sources 100 into the standardisation models 200, from which data is extracted for delivery to reports and/or databases by the data delivery components 300.

In more detail, the specific nature of the data in the three categories (a) to (c) above is as follows:

(a) Clinical Data: Patient data captured during the life of a clinical trial that is used to assess the safety and efficacy of a product, compound or treatment. Clinical data includes data from case report forms ("CRFs"), laboratory results, patient diaries, and imaging data. Clinical data is captured and delivered through disparate systems, and must be conformed, reconciled and checked for completeness as part of the clinical data management process.

(b) Clinical Study Properties: Includes properties such as study start up details, planned events and procedures and study close details (c) Clinical Reference Tables: Includes reference data such as adverse events of special interest, and disallowed concomitant medications.

The SDM 4 aids the process of conforming data (also referred to as data mapping) by providing user interfaces, metadata, and other supporting tools for these transformations. The integration and standardisation of clinical data in clinical data records ("CDRs") by the SDM 4 reduces the prior art duplication of data manipulation work and increases operational efficiency by enabling standards-driven data processing and provision.

The mapping method allows centralisation and standardisation of data processing and data access using:

A mapset, which is defined as the set of one or more table maps—or mapping specifications—that specify how data for a particular study will be transformed into a standard set of target tables.

A central repository of metadata that includes information about study source data structures, standard target structures, and other supporting data.

Functions with an interface that allows the user to capture the mapset and to record the transformation logic (also referred to as "mapping") between study source data and target data structures.

Functions with an interface that supports an iterative dual mapping process with two data mappers performing the same mapping and a mapping reviewer generating a detailed report of the differences between two different mappings.

A central library of pre-defined mapping functions that can be applied to one or more variables. A registry of functions is maintained within the metadata repository to support the extension of this library over time.

A central repository of metadata describing the mapping logic between targets and sources.

An interface to support completeness/consistency checks for a mapset that includes checks for incomplete or inconsistent mappings.

Figure 5:
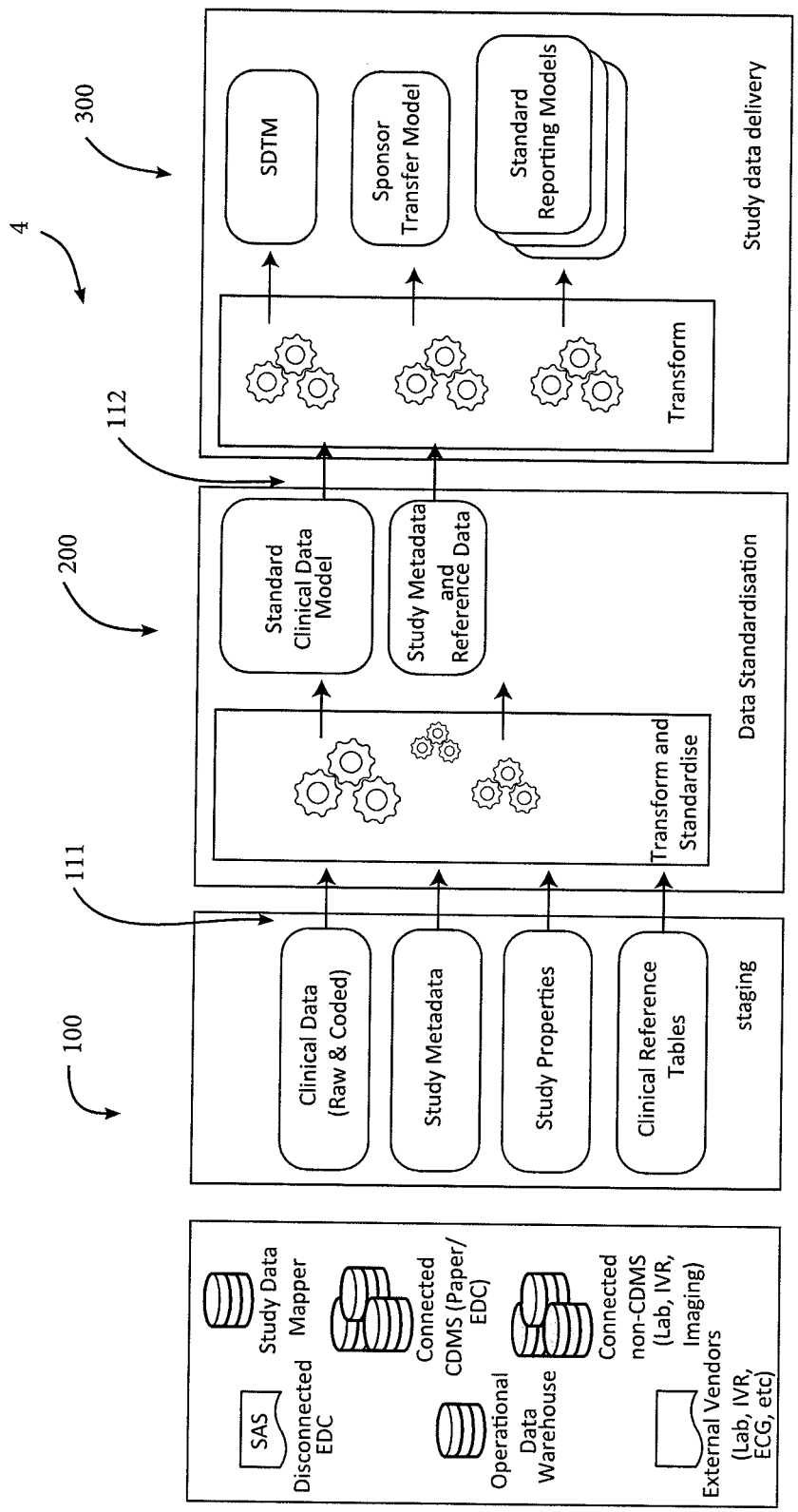
FIG. 5 is a more detailed diagram of the main flows for a data mapping method including source data systems and data transformation code.

A SAS, PL/SQL, or Oracle Life Sciences Data Hub ("LSH") code and program generation engine that automatically generates the ETL programs that transform the data into the standard structures (FIG. 5) based on the captured mapping metadata. These generated ETL programs are stored in metadata.

A pattern matching engine that provides a search function to identify existing, approved maps that are potential exact or partial matches for the selected target domain table Interfaces to support integration with LSH.

One aspect of the SDM 4 is that it adds efficiency to the process of transforming clinical data to a set of standard structures, without sacrificing data integrity. To facilitate that goal, the SDM includes at least one mapset, which is defined as the set of one or more table maps—or mapping specifications—that specify how data for a particular clinical study will be transformed into a standard set of target domain tables. This structure of logical target structures support efficiency and reusability across target structures and studies by identifying mapping elements that—once defined and verified as correct—can be copied as-is to other mapsets.

Figure 6:
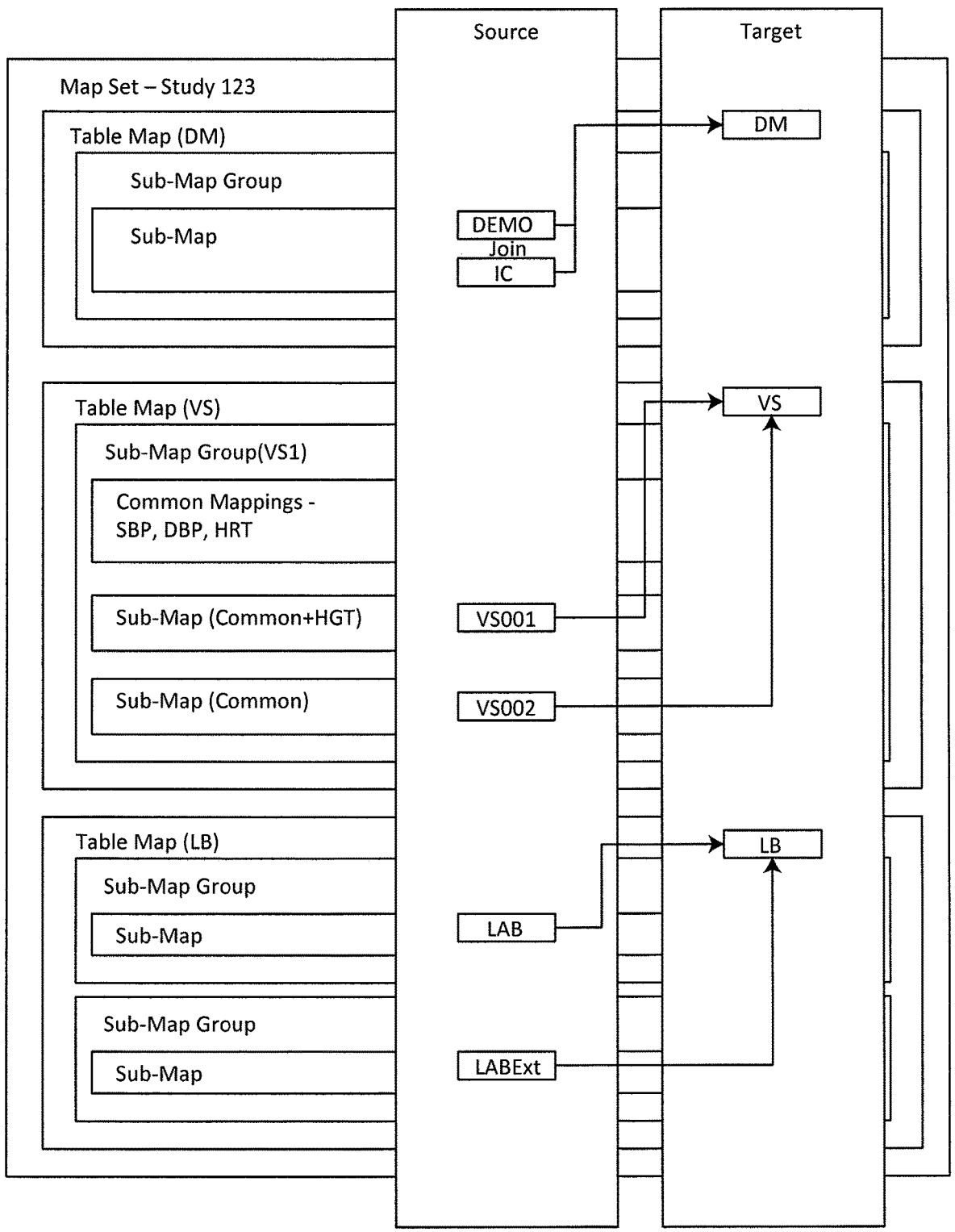
FIG. 6 details mapping methods including a common table mapping method, in which a mapset includes multiple table maps.
Figure 7:
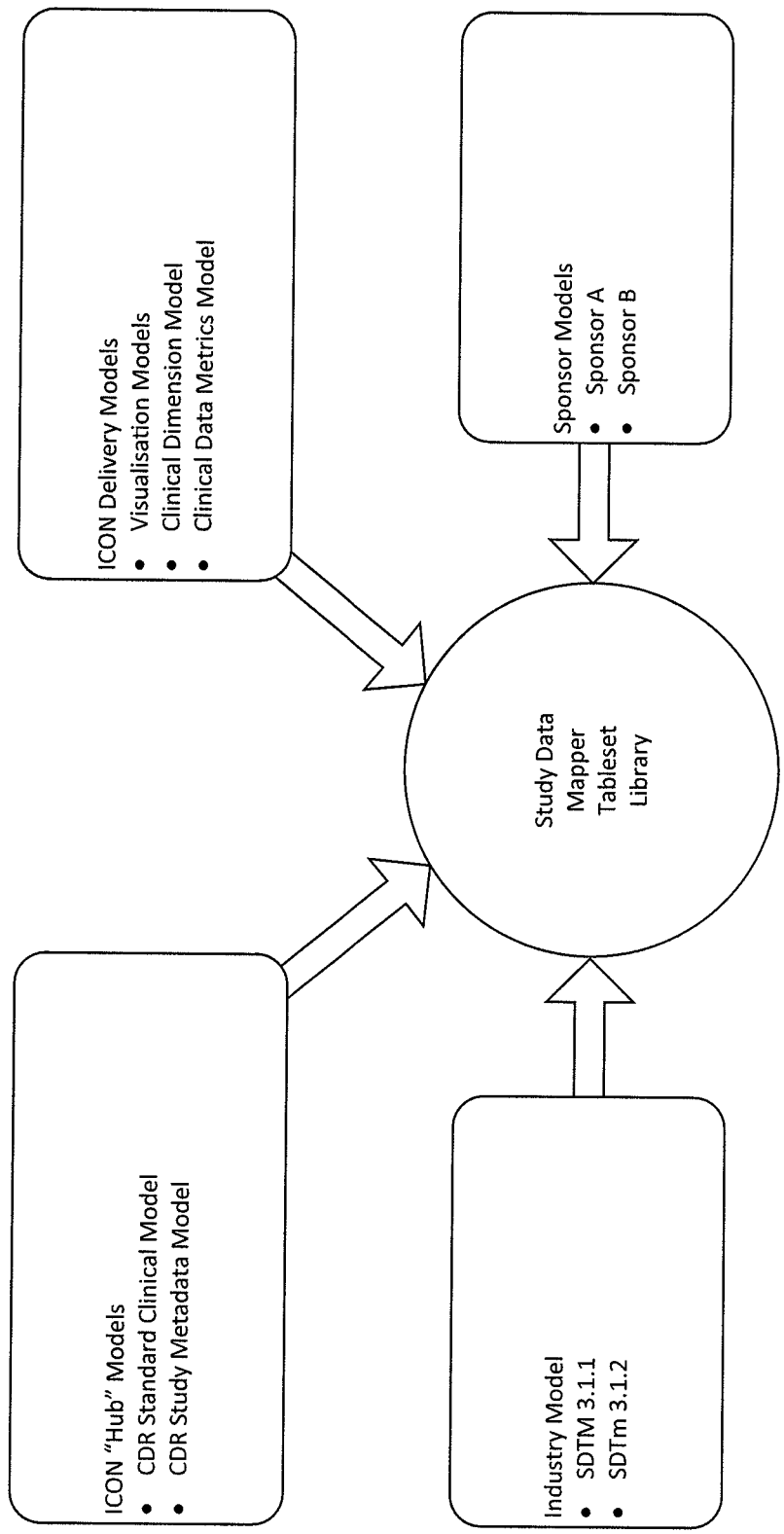
FIG. 7 shows use of data models in the method, these models being part of a data standardisation layer which receives the output of the mapping method.

FIG. 6 illustrates the logical structure of a study mapset. The following table defines these structures and other components of the SDM which are involved in the mapping process.

| Acronym/Term | Description |
|---|---|
| In-line Operation | An in-line operation is a function that can be applied to a source variable to transform it to the value expected by the target variable. For example, if the user applied the in-line operation DATE_TO_ISO to a date source variable, the target variable would then contain that date transformed to the ISO 8601 format. An in-line operation supports both SAS and PL/SQL and is registered in the system for use in mapping specifications. |
| Mapping Project | A mapping project is the highest level of organization in the SDM 4. It defines the set of source tables that will be mapped to a set of target tables, and (2) the mapset that will contain the mapping specifications. A mapping project can be used to define source study tables to support raw study data—source study definition—or can be the set tables that define a target standard data model—a target structures definition. This allows the user to specify not only how raw study data can |

-continued

| Acronym/Term | Description |
| --- | --- |
| | be transformed into a target standard definition but also how the tables in one target standard definition can be transformed into a different target standard definition. |
| Mapset | A mapset is the collection of one or more table maps that specify how data for a study will be transformed into a standard set of target tables. |
| Tableset | A tableset defines the collection of tables (both source and target) and value lists that can be used in a mapset. |
| Source Table | A source table is any data table that will be transformed to a target table. A source table may contain raw study data or it may contain study data that was previously transformed. |
| Sub-map | A sub-map is the portion of a sub-map group that defines how data stored in a single target table can be traced back to the original data in a one or more source tables. A sub-map's type (i.e., common, single, or multiple) defines the table variables that will be mapped in that sub-map. |
| Sub-map Alias | A sub-map alias identifies how a particular sub-map relates to the set of variables that are contained in common sub-map. |
| Sub-map Group | A sub-map group is the set of all mapping specifications from one or more source tables to a single target table. |
| Table Map | A table map defines the set of source tables that contribute to the selected target table. A table map will consist of one or more sub-map groups. |
| Tableset | A tableset is the list of source and target tables that are assigned to a Mapset. |
| Target Table | A target table is the table that will contain logically related data—demographics, vital signs, and adverse events—that has been transformed into a standard format and structure. |
| Transform/ Transformation | Transformation is the process of using rules, in-line operations, and value lists to convert variables in one or more source tables to the format and structure of a specified target table. |
| Value List | A value list is any pre-defined list of values that the user can choose from when using the study data mapper system. |
| Value List Table Pair | A value list table pair is the combination value list tables (source and target) to be associated when converting a source study to a target standard definition or when converting between two target standard definitions. The mapping of the two value lists identifies how to translate data from the source value list to the target value list. |
| Variable | A data column, field, property, or attribute. Tables (both source and target) and value lists are composed of variables. |

Standards Metadata

The SDM 4 uses a central repository of metadata in the data standardisation layer, that for target data models includes metadata related to: tables, table variables, value lists, value list values, version attributes (author, approver, version number, validation status, etc.) and search tags (e.g., therapeutic area, sponsor, etc.). This metadata can come from a variety of sources (for example text files, spreadsheets, databases, and datasets).

The standards development lifecycle of the standard data models is managed by the SDM 4. In cases where the models do not support a study-level variable or table, an additional variable or table may be added to the study-level model by the SDM 4. This extension must be approved by a mapping reviewer before the variable or table can be used in production. These additions may be elevated to the standards team to decide if the variable/table is a valid candidate to be added to the standard model. The SDM 4 metadata repository is accessible to LSH transform programs and LSH automation programs.

Figure 8:
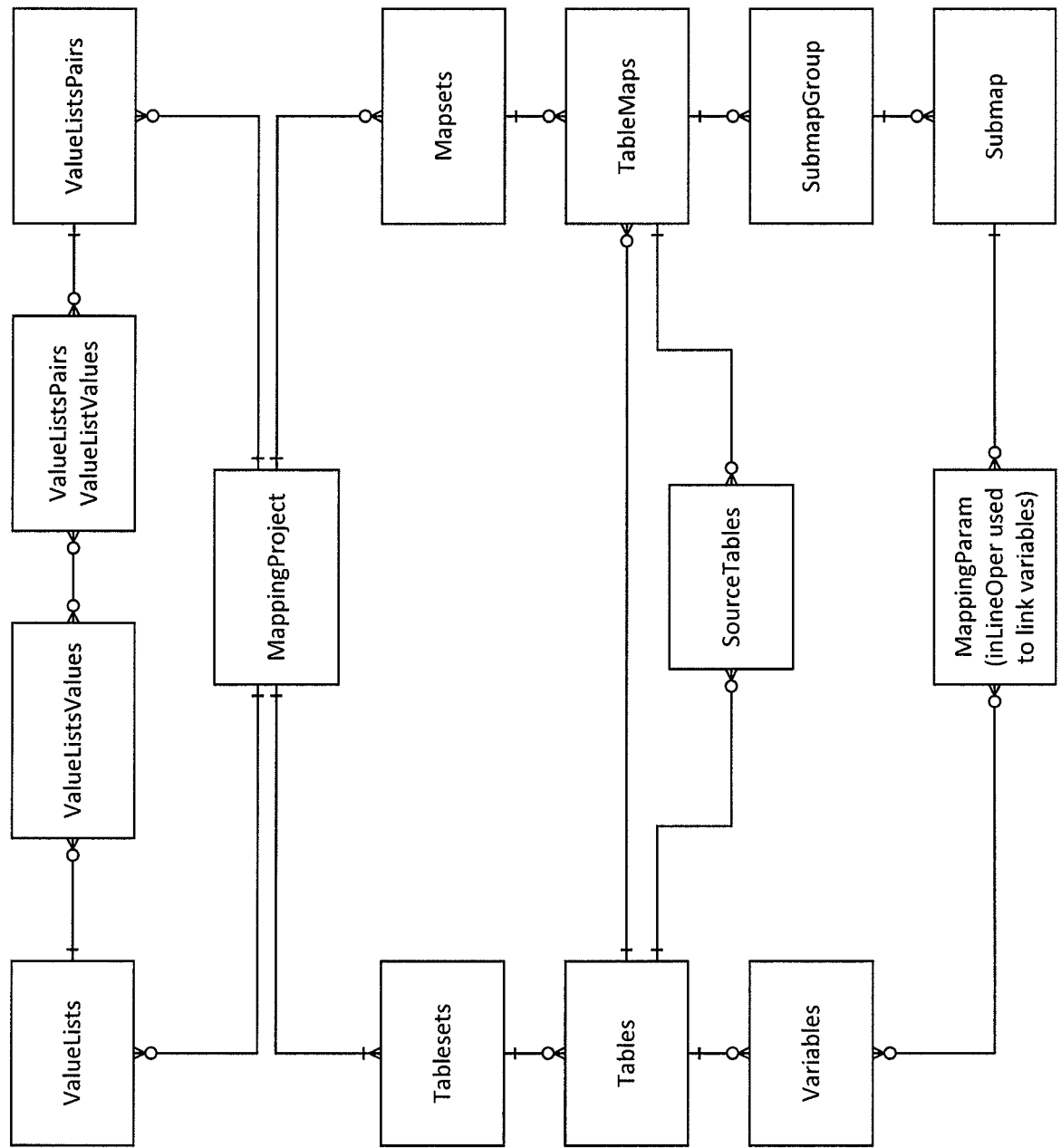
FIG. 8 is a diagram showing object inheritance of the study data mapper.

There are many tables which comprise the study data mapper. They are used to contain the metadata for the structures of studies and standards as well as the mapping between studies and standards as well as between one standard and another. FIG. 8 is an ERD diagram of the major components. A mapping project receives a feed from the contained objects of value lists, and value list values and pairs. A source table object is linked with tables and table maps, and a mapping parameters object is linked with variable and sub-map objects.

Mapping Recommendations

To promote map reusability across studies, the system 1 provides a search function to identify existing maps that are potential exact or partial matches for the selected target table. To promote the reuse of mapping specifications across studies, mapsets are organized at a sufficiently granular level so that groups of variables are reusable both within and across mapsets. The map search function allows the user to return partial matches according to a combination of the metadata tags, including a sponsor, a therapeutic area; and a source system.

The system 1 provides a user-configurable weighting system to assign relative weights to table and variable attributes. The search function for partial matches allows the author to specify a threshold for variable matches, for example, a match across 35% of the variables or 74% of the variables. The system automatically pre-populates the mapping specification interface with the appropriate set of maps and study variables for the study that was selected from the search results. The system also provides functionality that allows the user to see the details of how a particular mapping is matched by the mapping recommendation. For example, the system can show which column matched by name, data type, length, precision or other attributes.

Common Mappings

The SDM 4 is programmed to map from one or more source structures to a target table structure. This is called a table map. In cases where there need to be multiple combinations of sources that are mapped to a single target in different ways then it should be possible to create multiple maps to the same target. These are called submaps. When there are variables in the separate submaps that are named the same and are mapped the same way then they can be mapped once in a common mapping and will be applied to each submap within the sub map group. This will reduce the overall effort to prepare table maps.

For example, given source table ST1 containing columns SC1, SC2, SC3, another source table ST2 containing columns SC1, SC2, and SC3 and a target table containing columns TC1, TC2, and TC3. The system can map SC1 to TC1 and SC2 to TC2 in a common mapping. In the individual sub maps SM1 and SM2, the system would allow for SC3 to map to TC3 and SC4 to map to TC3 respectively. A table alias is used in the common mapping and then is resolved to ST1 in SM1 and SC2 in SM2. The resultant code would union the results as if the common mapping had been applied individually to both SM1 and SM2. FIG. 6 shows another use case of common mappings for the VS table map.

Parallel Mappings and Validation

Figure 9:
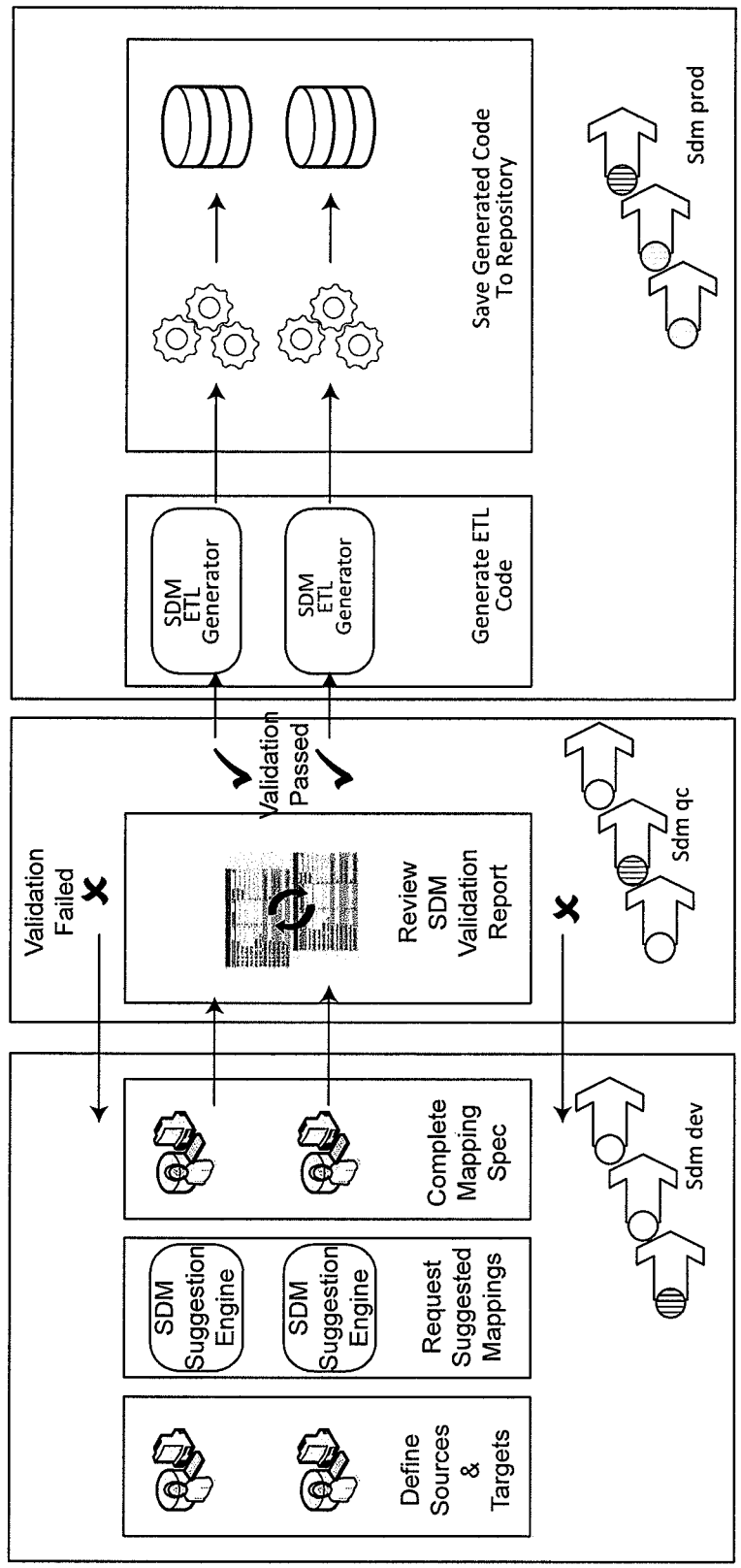
FIG. 9 is a flow diagram illustrating implementation of a double mapping process as part of the mapping phase.

The SDM 4 implements a parallel mapping process (also referred to as "double mapping") in which two SDM instances independently specify the transformations to be applied as part of the mapping process (FIG. 9).

Once the parallel maps are ready for validation, a mapping reviewer function generates a detailed report of the differences between two different mapsets, including a detailed report on the compliance of a study mapset with its selected standard(s). The mapping reviewer can release each map in a mapset as soon as it is complete, or it can release an entire mapset when its component maps are complete.

Audit Trail

The primary audit mechanism for the system is to maintain and track multiple versions of mapping project entities (mapsets, tablesets, etc.). These entities are maintained within the system database, recording the state of the data for a specific version of tablesets, tables, variables, tablemaps, sub-map groups, and sub-maps. This provides the ability to reconstruct the state of the metadata for points in time for software and mapping specification spreadsheet generation. The multiple versions for the various entities are indicated in the user interface, showing the data/time stamps of the created date, modified date, and the user creating or modifying the entity (tableset, table, variable, etc.).

The SDM also logs database changes (un-versioned tables), capturing the person logged in to the SDM, the table being changed, the type of change (create, update, delete), the date/time of the change, the variable being changed, and the impacted variable value. Tables that are not versioned will record data into this audit table.

Mapping Process

The SDM 4 maps targets from source rather than the common prior art approach of mapping sources to targets. This focuses the user experience on the complete mapping data to the standard, and minimises the risk of inconsistent mappings to standards.

Figure 10:
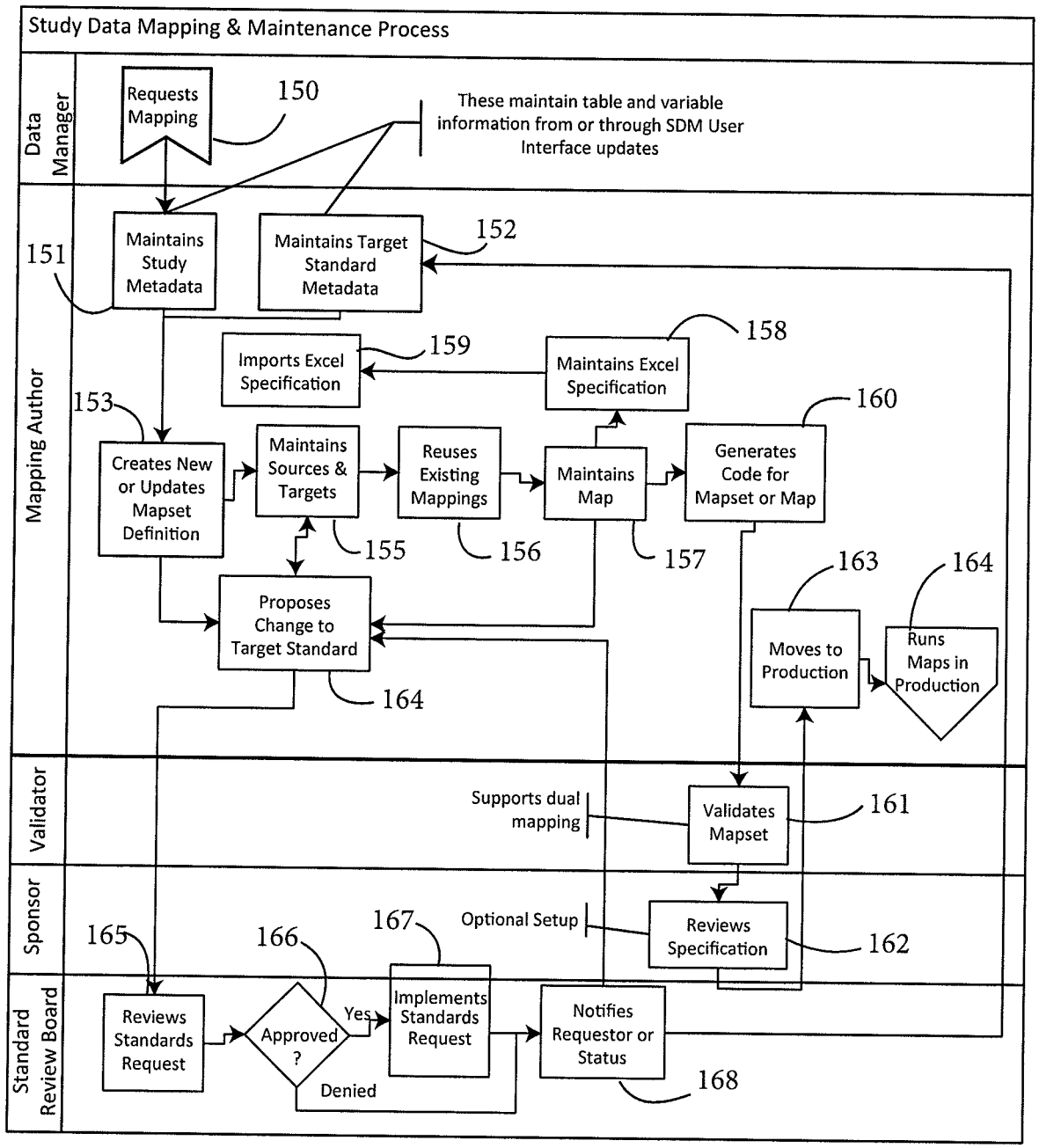
FIG. 10 is a more detailed flow diagram showing roles of systems involved in the mapping.
Figure 15:
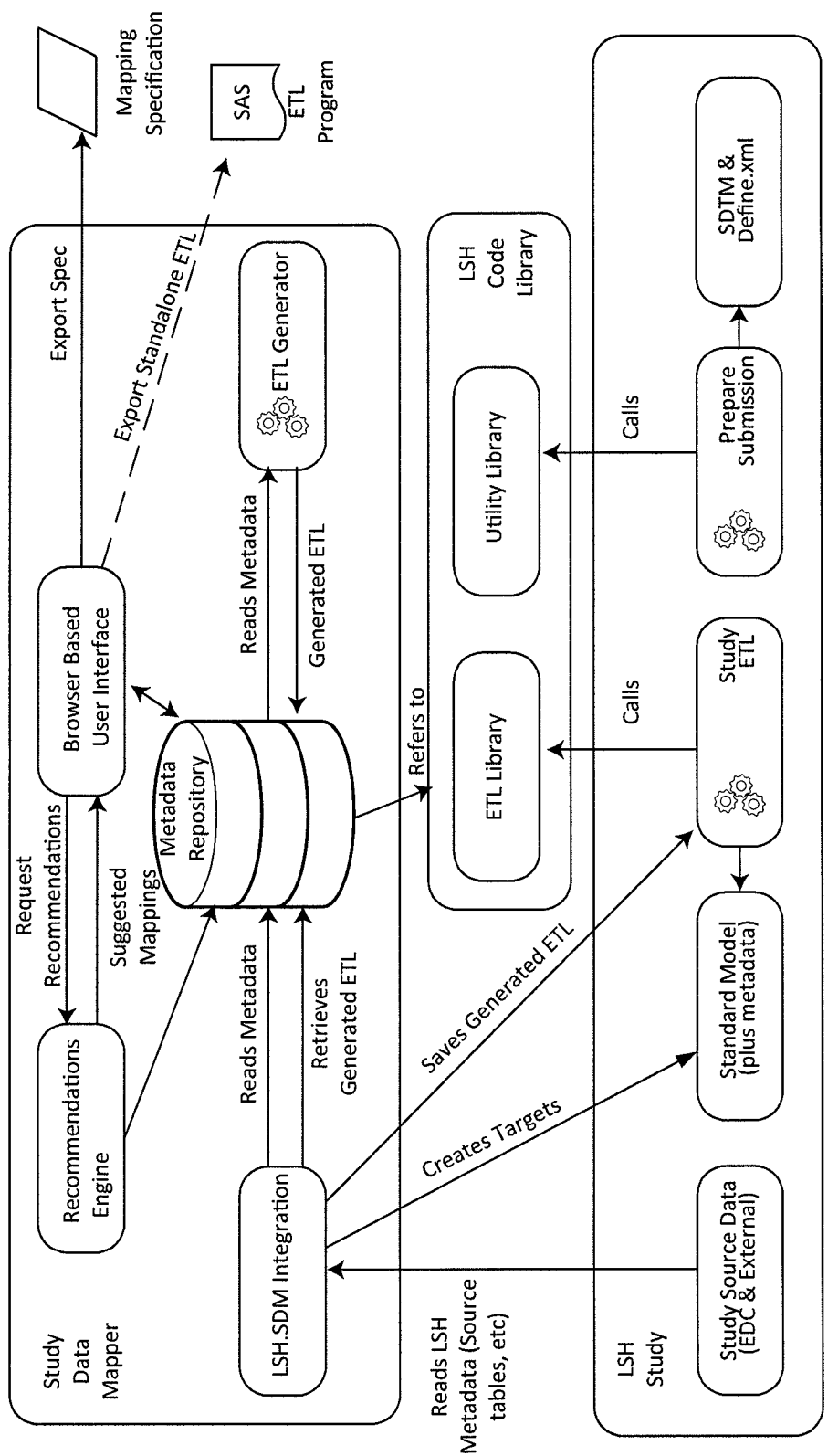
FIG. 15 is a more detailed flow diagram illustrating operation of the study data mapper, showing its interactions with the systems illustrated in FIG. 13.

Referring to FIG. 10, the process in one embodiment for study data mapping and maintenance is:

150. When the clinical design ("CRF") for the study is complete and the study team has a solid understanding of the study's data content and structure, the data manager function will manually request a new study mapset.
151. The SDM 4 uses a central repository of metadata that includes information about the source studies, the target structures, and other supporting data. This metadata can come from a variety of sources (for example text files, spreadsheets, databases, SAS datasets) and the mapping author function ensures that all metadata is loaded and maintained under version control.
152. When the mapping author receives a request for a new mapset, under user instruction it starts the SDM 4 and creates a new mapset by identifying the sponsor and study, setting key attributes (e.g., therapeutic area, source of the data, location of the source data), and selects the standard data model upon which the mapset will be based.
153. The mapping author with the appropriate privileges can implement allowed study-specific extensions to the target structures, such as adding new variables and making changes to length and precision of existing variables.
154. The mapset now contains all the information the mapping author function needs to begin the high-level mapping between the study's source tables and the target domain tables. It can, under user instruction, either import these high-level mappings from a spreadsheet or specify how one or more source tables will be linked to each of the target domain tables.
155. The mapping author function specifies a set of search criteria to search for and reuse existing, approved mapping specifications. It can either copy some or all of the maps from an existing mapset or can copy maps from one or more mapsets. Copying existing maps to the mapset automatically populates the mapset with each complete map and its metadata, specifications, etc.
156. Each mapset is structured in such a way that one or more mapping authors can work on the mapping specifications at the same time. Each mapping author can maintain the mapping specifications for one or more table mappings and validate his work periodically to ensure his table mappings meet all requirements.

The mapping author maintains the mapping tables and specifications by:
Adding, updating, or deleting the relationships between sources and targets
Adjusting the source and target variables
Mapping the source variables to the target variables
Applying in-line operations that conform the source variables to the target variables
Applying code list mappings 157. During the development process the mapping author can generate the programs for either an entire mapset or for any subset of table mappings.
158. (and 160) The mapping author may be developing table mappings outside the system in a spreadsheet. In that case, it imports those specifications into the SDM 4 when they are complete and are ready for final testing. This can be an iterative process as the mapping author continues to refine the table mappings over time.
161. The SDM 4 supports two parallel mappings (mapsets) for a specific study and allows the mapping author or a validator function to produce comparison reports of two different mapsets to verify that the clinical study requirements are satisfied or identify revisions that are needed. When the entire mapset has been verified, the validator can optionally send the appropriate mapping specifications to the sponsor for external review (if requested by the clinical study sponsor).
162. If requested by the sponsor, the sponsor reviews the mapping specifications, verifies that all requirements for the study are met, either approves the mapset or identifies any required changes.
163. When both the sponsor (optionally) and the validator have approved the mapset, the mapping author updates the mapset status, moves the mapset version to production, and moves the ETL programs to production.
164. All ETL programs for the mapset are ready to be run and can be scheduled for execution.
165. A report can be prepared showing all of the extensions made to the target standard. This can be used for consideration in reviewing the target structures to see if they should be enhanced.
166. The standards review board can utilize the prepared reports.
167. The standards review board can identify changes to the target structures based upon provided reports and notify the mapping author of desired changes.
168. The standards review board notifies the mapping author of needed additions or changes to the target structures, regardless of the source of enhancement requests.

The transform code in FIG. 11 is an example of SDM 4 generated code. For this example the end user supplied the specification in FIG. 14 through the system interface.

Summary Actors and Actions

FIG. 13 shows the systems that interact with the SDM 4, including:

LSH, which serves as the central repository for target data standards including metadata target structures, and PL/SQL programs that are generated by the SDM to transform the raw clinical data to target standard data tables stored in the subject data hub (SDH).

A shared file system, which stores secondary mapset outputs generated by the SDM.

The SDM generates several types of mapset outputs, and these outputs are stored by type in one of the three primary subsystems; the study data mapper subsystem, and the LSH subsystem and shared file subsystem.

The following user actors interact with the SDM 4(FIG. 14):

Data Manager—Initiates a new mapping specification

Mapping Author—Loads metadata into the SDM; uses the SDM to create and maintain the mapping specifications (including retiring elements of the mapping specification no longer needed); generates the Mapset outputs; may extend target structures to meet study needs; and moves approved ETL programs into production Validator—Generates, reviews comparison of, and verifies the Mapset outputs Sponsor—Reviews and approves or rejects the mapping specifications, if specifically requested Standards Review Board—Uses Target Extension reports to identify potential changes to target structures; communicates evolving changes to target structures The user actors interact with the system to assist the system to perform the following tasks.

| Data Manager |
| --- |
| Task |
| Informs Mapping Author that mapping can begin |

| Mapping Author |
| --- |
| Task |
| Maintains study and target structures metadata |
| Creates Mapsets and selects study and target structures metadata |
| Creates and maintains mapping specifications (including marking items for removal - soft delete) |
| Imports, exports, and maintains Excel specifications |
| Extends target structures using approved extension methods to meet study needs |
| Generates Mapset code |
| Moves approved mapping programs to production after Validator completes review |
| Runs mapping programs in production |

| Validator |
| --- |
| Task |
| Generates comparison of Dual Mapsets for review to see if the mappings satisfy ICON requirements |
| If needed, communicates needed changes to Mapping Author(s) |
| Identifies mapping of choice from dual mapping and notifies Mapping Author |
| Optionally sends mapping specifications to Sponsor for review if requested |
| Validates that mapping satisfies ICON requirements |

| Sponsor |
| --- |
| Task |
| Upon Sponsor Request, reviews and approves/rejects mapping specifications sent to them by Validator. Note that all interactions are between Validator and Sponsor outside of SDM; there are no direct SDM interactions by the Sponsor. This is an external process supported by reporting produced by SDM. |
| Receives final Mapset (no direct SDM interaction) |

| Standards Review Board |
| --- |
| Task |
| Receives Target structures extension reports |
| Communicates Target Standard evolutionary changes to Mapping Author |

It will be appreciated that the invention provides for highly automated data processing while maintaining data integrity despite the fact that the source data can be from a variety of different sources and the many processing requirements required for clinical data. The invention achieves the following benefits in use:

Acquires and processes clinical trial data in a standardized manner.

Selects sites for clinical trials, matching a site's performance profile.

Tracks clinical trial safety.

Tracks site performance, ranking high and low performing sites.

Matches centralized and onsite site activity to sites by their performance information and performance trending history.

Using standardized data, a trial is automatically evaluated from a scientific, safety and quality perspective across an entire compound or a single study.

The invention is not limited to the embodiments described but may be varied in construction and detail.

The invention claimed is:

1. A clinical data management system comprising:
a plurality of staging databases comprising clinical study level staging databases and pooled cross-study databases storing clinical data, study metadata, study properties, and clinical reference tables;
a plurality of distributed digital data processing servers configured to import and adapt source data from disparate clinical site sources into the staging databases at refresh intervals of uniform frequency, wherein the distributed digital data processing servers capture and maintain an audit trail of source data imported into the staging databases;
user interfaces and external system interfaces comprising a plurality of input modules for enabling a user of the system to input one or more study-specific changes to data model standards and mapsets and a plurality of delivery and visualization modules configured for reporting and displaying processed clinical study data mapped into the staging databases; and
a study data mapper that maintains a plurality of data models comprising a study metadata model, a clinical data model, a discrepancy data model, and a reporting support data model, wherein the study data mapper is configured to:
map data from the staging databases into the data models, and map data from the data models into data delivery databases, wherein the data models act as consistent core data structures of data across said disparate clinical site sources, said consistent core data structures allowing for study-specific additions but not allowing for destructive changes to core variables or tables; and perform said mapping into the data models by using metadata defining the data models for transforming data from each staging database to one or more data models according to one or more mapsets, wherein each mapset specifies how data for a clinical study is to be transformed into a standard set of target tables.

2. The clinical data management system as claimed in claim 1, wherein the mapper inserts extensions to date fields where imputations are required for incomplete or invalid dates and wherein the mapper provides in each table of the data models a primary key and a surrogate key, in which a primary key is a combination of columns or rows which define the uniqueness of a record within a table, and a column or row which is a member of a primary key cannot contain null values.

3. The clinical data management system as claimed in claim 1, wherein the mapper defines primary keys within the data models as mutable, in which the data values stored in the constituent variables may change, and in which a surrogate key is a single row or column that uniquely identifies a record in a table and are immutable and cannot contain null values.

4. The clinical data management system as claimed in claim 1 wherein the data models are in a hierarchy consisting of three levels; first and second levels of standard models and a third level for study implementation, and wherein the first level includes version-controlled metadata definitions of core data models, the second level includes metadata definitions of sponsor standard data models, and the third level includes study execution physical data models, and wherein the data models include a study metadata model containing study level metadata describing study design and planning, and also clinical reference tables.

5. The clinical data management system as claimed in claim 1, wherein the data models include a clinical data visualisation model including a study-level standard reporting structure for data visualisation through third party reporting tools, and wherein a data model includes a subject snapshot table, said subject snapshot table containing a row for each clinical trial patient, describing their current status and progress to date in the study, with a combination of demography data, disposition or milestone data, eligibility data, and safety data.

6. The clinical data management system as claimed in claim 1, wherein the metadata is in a metadata model.

7. The clinical data management system as claimed in claim 1, wherein the data models include a clinical data visualisation model including a study-level standard reporting structure for data visualisation through third party reporting tools, and wherein a data model includes a subject snapshot table, said subject snapshot table containing a row for each clinical trial patient, describing their current status and progress to date in the study, with a combination of demography data, disposition or milestone data, eligibility data, and safety data; and wherein the mapper performs two transformations according to the same mapset, compare resultant target data, and provide feedback, and wherein at least two mapper software instances independently specify transformations to be applied as part of the mapping process, and a mapping reviewer function automatically generates a detailed report of the differences between two different specified transformations, and wherein the source data is clinical study data and the reviewer generates a detailed report on the compliance mapping with its selected standards.

8. The clinical data management system as claimed in claim 7, wherein the mapping reviewer releases each map in a mapset as soon as it is complete, and releases an entire mapset when its component maps are complete; and wherein the metadata comprises a library of pre-defined mapping functions that can be applied to variables; and wherein the metadata is used to automatically generate mapping software functions, and wherein each mapset has an associated set of source and target tables; wherein a mapset defines transformation of source variables, said variables including data, fields, properties, attributes, and table value lists; and wherein the transformation step maps targets to a source.

9. The clinical data management system as claimed in claim 1, wherein the mapper performs the step of mapping from one or more source structures to a target structure according to a table map; wherein there are multiple combinations of source structures that are mapped to a single target structure and the method creates multiple maps to the same target, called submaps; wherein common variables in separate submaps are named the same and have the same mapping requirements, and these common variables are mapped the same way in a common mapping and are applied to each submap within a sub map group.

10. The clinical data management system as claimed in claim 1, wherein a search engine identifies similar previously mapped table structures as exact or partial matches, and wherein the system performs the step of applying system installation configurable attributes or tags to mapping projects, table sets, value lists, variables, table maps, submaps, or variable maps that can then be used for searching and reporting on any of said entities, and wherein code is generated in multiple languages for the same mappings giving the same resultant data.

11. The clinical data management system of claim 1, wherein the mapper is further configured to:
determine the compliance of the clinical data model with clinical data model standards; and
electronically transmit non-compliant data into the discrepancy data model.

12. The clinical data management system of claim 1, wherein the mapper is further configured to:
add unique identifiers to data model tables to identify change deltas; add original code and decode values to data model tables;
add data status flags to the data models to assist status and query management; and
insert a source reference field into said data models to provide traceability from said clinical site sources to the data models.

13. The clinical data management system of claim 12, wherein the mapper is further configured to:
determine the compliance of the clinical data model with clinical data model standards; and
electronically transmit non-compliant data into the discrepancy data model.

14. The clinical data management system of claim 12, wherein the mapper is further configured to:
add unique identifiers to data model tables to identify change deltas; add original code and decode values to data model tables;
add data status flags to the data models to assist status and query management; and insert a source reference field into said data models to provide traceability from said clinical site sources to the data models.

15. The clinical data management system of claim 1, wherein one or more tables of the clinical data models includes a primary key and a surrogate key, in which the primary key defines the uniqueness of record within a table.

16. A computer readable medium comprising non-transitory software code to perform the following steps when executed by a digital processor:
   importing and adapting source data from disparate clinical site sources into the staging databases at refresh intervals of uniform frequency, wherein the distributed digital data processing servers capture and maintain an audit trail of source data imported into the staging databases;
   receiving one or more study-specific changes to data model standards and mapsets;
   reporting and displaying processed clinical study data mapped into the staging databases;
   maintaining a plurality of data models comprising a study metadata model, a clinical data model, a discrepancy data model, and a reporting support data model; and
   maintaining a study data mapper that is configured to:
      map data from staging databases into the data models, said staging databases including clinical study level staging databases and also pooled cross-study databases storing clinical data, study metadata, study properties, and clinical reference tables, and mapping data from the data models into data delivery databases, wherein the data models act as consistent core data structures of data across said disparate clinical site sources, said consistent core data structures allowing for study-specific additions but not allowing for destructive changes to core variables or tables; and
      perform said mapping into the data models by using metadata defining the data models for transforming data from each staging database to one or more data models according to one or more mapsets, wherein each mapset specifies how data for a clinical study is to be transformed into a standard set of target tables.

17. The computer readable medium of claim 16, wherein the mapper is further configured to:
   determine the compliance of the clinical data model with clinical data model standards; and
   electronically transmit non-compliant data into the discrepancy data model.

18. The computer readable medium of claim 16, wherein the mapper is further configured to:
   add unique identifiers to data model tables to identify change deltas; add original code and decode values to data model tables;
   add data status flags to the data models to assist status and query management; and
   insert a source reference field into said data models to provide traceability from said clinical site sources to the data models.

19. A clinical data management system comprising:
   at least one digital data processor,
   user interfaces and external system interfaces,
   at least one database,
   at least one distributed digital data processing server, and
   a study data mapper,
   wherein the digital data processor imports and adapts source data from disparate clinical site sources into staging databases at refresh intervals of uniform frequency and captures and maintains an audit trail of source data imported into the staging databases;
   wherein the user interfaces and external system interfaces comprise a plurality of input modules for enabling a user of the system to input one or more study-specific changes to data model standards and mapsets and a plurality of delivery and visualization modules configured for reporting and displaying processed clinical study data mapped into the staging databases;
   wherein the database comprises of clinical study level staging databases and pooled cross-study databases storing clinical data, study metadata, study properties, and clinical reference tables;
   wherein the study data mapper is configured to:
      maintain a plurality of data models, and map data from the staging databases into the data models, and maps data from the data models into data delivery databases, wherein the data models act as consistent core data structures of data across said disparate clinical site sources, said consistent core data structures allowing for study-specific additions but not allowing for destructive changes to core variables or tables, and said data models include a study metadata model, a clinical data model, a discrepancy data model, and a reporting support data model; and
      perform said mapping into the data models by using metadata defining the data models for transforming data from each staging database to one or more data models according to one or more mapsets, wherein each mapset specifies how data for a clinical study is to be transformed into a standard set of target tables.

20. A method of managing clinical data using a plurality of staging databases, a plurality of distributed digital data processing servers, a plurality of user interfaces and external system interfaces, and a study data mapper that maintains a plurality of data models, the method comprising:
   mapping data from the staging databases into one or more data models, the data models including one or more of a study metadata model, a clinical data model, a discrepancy data model, and a reporting support data model;
   mapping data from one or more of the data models into data delivery databases, wherein the data models act as consistent core data structures of data across disparate clinical site sources, said consistent core data structures allowing for study-specific additions but not allowing for destructive changes to core variables or tables;
   wherein the mapping uses metadata defining the data models for transforming data from each staging database to one or more data models according to one or more mapsets, wherein each mapset specifies how data for a clinical study is to be transformed into a standard set of target tables,
   electronically transmitting data from one or more staging databases into the clinical data models, wherein each table of the clinical data models includes a primary key and a surrogate key, in which the primary key defines he uniqueness of a record within a table;
   determining the compliance of the clinical data model with a received clinical data model standard; and
   electronically transmitting any non-compliant data into the discrepancy data model.

21. The method of claim 20, further comprising one or more of:
   adding unique identifiers to data model tables to identify change deltas;

adding original code and decode values to data model tables;

adding data status flags to the data models to assist status and query management; and inserting a source reference field into said data models to provide traceability from said clinical site sources to the data models.

22. The method of claim 20, further comprising one or more of:

receiving, using user interfaces and external system interfaces comprising a plurality of input modules, any one or more study-specific changes to data model standards and mapsets; and reporting or displaying, using the plurality of delivery and visualization modules, processed clinical study data mapped into the staging databases.

\* \* \* \* \*